United States Patent [19]
Edmundson et al.

[11] Patent Number: 5,654,334
[45] Date of Patent: Aug. 5, 1997

[54] ANALGESIC USE OF N-L-α-ASPARTYL-L-PHENYLALANINE 1-METHYL ESTER

[75] Inventors: Allen B. Edmundson; Carl V. Manion, both of Oklahoma City, Okla.

[73] Assignee: Oklahoma Medical Research Foundation, Oklahoma City, Okla.

[21] Appl. No.: 590,409

[22] Filed: Jan. 25, 1996

Related U.S. Application Data

[60] Provisional application No. 60/000,479, Jun. 23, 1995.
[51] Int. Cl.$^6$ ................................................. A61K 31/24
[52] U.S. Cl. ................................................. 514/538
[58] Field of Search ..................................... 514/538

[56] References Cited

U.S. PATENT DOCUMENTS

| | | | |
|---|---|---|---|
| 3,492,131 | 1/1970 | Schlatter | 99/141 |
| 4,689,218 | 8/1987 | Gazzaniga et al. | 424/43 |
| 5,053,393 | 10/1991 | Tjoeng | 514/18 |
| 5,053,396 | 10/1991 | Blass | 514/45 |
| 5,496,856 | 3/1996 | Creppy | 514/566 |

FOREIGN PATENT DOCUMENTS

| | | | |
|---|---|---|---|
| 0468121 | 1/1992 | European Pat. Off. | A61K 9/18 |
| 1207232 | 8/1989 | Japan | A61K 31/195 |
| 2279250 | 4/1995 | United Kingdom | A61K 31/19 |
| 8807892 | 10/1988 | WIPO . | |
| WO9514486 | 6/1995 | WIPO . | |
| WO9516457 | 6/1995 | WIPO . | |

OTHER PUBLICATIONS

Leon et al., "Safety of Long-term Large Doses of Aspartame", *Archives of Internal Medicine*, 149, pp. 2318–2324 1989.

Douglas, W.W., "Polypeptides–angiotensin, plasma kinins, and other vasoactive agents; prostaglandins," *The Pharmacological Basis of Therapeutics*, 5th ed., L. S. Goodman and A. Gilman (eds.), MacMillan Publishing Co., Inc., New York, p. 647 (1975).

Guiso, et al., "Effect of tyrosine on the potentiation by aspartame and phenylalanine of metrazol–induced convulsions in rats," *Fd Chem Toxic* 29:855–857 (1991).

Insel, Paul, "Analgesic–antipyretic and antiinflammatory agents and drugs employed in the treatment of gout," *The Pharmacological Basis of Therapeutics*, 9th ed., J. G. Hardman and L.E. Limbird (eds.), McGraw–Hill Companies, Inc., New York, pp. 620–622 (1996).

Picot, et al., "The x–ray crystal structure of the membrane protein prostaglandin $H_2$ synthase–1," *Nature* 367:243–249 (1991).

*Primary Examiner*—Raymond Henley, III
*Attorney, Agent, or Firm*—Sidley & Austin

[57] ABSTRACT

N-L-α-aspartyl-L-phenylalanine 1-methyl ester and/or its derivatives has been found to have analgesic pain relieving properties. It has been found to be especially effective in relieving pain associated with osteoarthritis and multiple sclerosis. It can be administered by itself or in combination with other analgesics. When given in combination with other analgesics, N-L-α-aspartyl-L-phenylalanine 1-methyl ester and/or its derivatives helps to alleviate the detrimental side effects of other analgesic medications by lowering the dosage requirements for pain relief.

14 Claims, 8 Drawing Sheets

ANALGESIC USE OF N-L-α-ASPARTYL-L-PHENYLALANINE 1-METHYL ESTER

CROSS REFERENCE TO RELATED APPLICATIONS

This application claims the benefit of prior filed copending U.S. Provisional Application Ser. No. 60/000479 filed Jun. 23, 1995.

TECHNICAL FIELD

The present invention relates to pain relieving composition and a method for use.

BACKGROUND OF THE INVENTION

Pain is the most common symptom for which patients seek medical assistance. In the case of incurable diseases, treatment for pain may last for extended periods of time. Pain is both a physical and an emotional experience which differs greatly from one individual to another. Although subjective, most pain is associated with tissue damage and has a physiological basis.

Pain can be either acute or chronic. Acute pain is generally caused by sudden injury, tissue damage, or infection for which the cause is easily found. Chronic pain, however, is the pain of pathological conditions and often difficult to isolate and treat. Chronic pain is routinely defined as pain of over six months duration.

For patients suffering from chronic pain, the autonomic nervous system adapts to the pain and evidences of autonomic hyperactivity such as tachycardia, hypertension, diaphoresis, mydriasis, and pallor disappear, leaving the physician to rely on the patient's subjective complaints in assessing chronic pain.

In the management of chronic pain, some types of pain permit treatment of the underlying disorder, i.e., radiation treatment for pain caused by bone cancer. In some cases, a particular treatment is given for a specific type of pain, i.e., treatment of trigeminal neuralgia or glossopharyngeal neuralgia with carbamazepine, reflex sympathetic dystrophies with local anesthetic, postherpetic neuralgia with direct stimulation.

In many patients, however, the pain is chronic and the physician can neither treat the underlying disturbance nor prescribe a specific therapy for that type of pain. For example, osteoarthritis is a joint disease characterized by degeneration and loss of articular cartilage and by osteophyte formation, or bony outgrowth of subchondral bone. The disease is slowly progressive, leading to chronic pain and stiffness and gradually to increasing dysfunction of the affected joint. The incidence of the disease increases with age and affects three times as many women as men.

Chronic joint pain, swelling, creaking, and stiffness are the most prominent symptoms of osteoarthritis. The disease commonly affects the distal interphalangeal joints of the hands, resulting in bone enlargements often accompanied by inflammation and pain. Weight bearing joints such as the neck, lower back, knees and hips are often affected by this type of arthritis.

Another major symptom of osteoarthritis is loss of articulation of the joint. Weakness and shrinkage of surrounding muscles may occur if pain prevents the joint from being used regularly. As movement of an affected joint becomes severely limited, the sufferer experiences loss of functionality of the joint. In the case of osteoarthritis of the hip or knees, ambulation becomes impaired.

Although osteoarthritis is the most common of the rheumatic diseases, its pathogenesis is not well understood, and currently there is no treatment that will retard or reverse pathological processes in the disease. The only treatment available to osteoarthritis sufferers has involved symptomatic treatment through analgesics for pain and nonsteroidal anti-inflammatory agents for reduction of joint inflammation. An injection of a corticosteroid may also be administered to a painful joint.

Chronic pain is also associated with multiple sclerosis (MS), also known as disseminated or insular sclerosis, a disease of the central nervous system (CNS) characterized by widespread patches of demyelination in the brain and spinal cord. The disease occurs worldwide in about 10–60 persons per 100,000 with the age at onset occurring at about 20–40 years, and appears to affect females more often than males. While MS is generally chronic and relapsing, fulminating attacks occur, and as many as 30% of the patients progress steadily from the onset.

Although multiple sclerosis is the most common demyelinating disease, its cause is unknown, and there is no treatment to retard or reverse the pathological processes of the disease. There is no specific therapy recommended because spontaneous remissions make treatment difficult to evaluate. The only treatment available to multiple sclerosis patients include corticosteroid therapy (e.g., prednisone or dexamethasone) until manifestations remit, and symptomatic treatment such as baclofen for spasticity and pain relievers such as analgesics and opiates.

There are several types of drugs used to decrease chronic pain. Analgesics are drugs used to decrease pain without causing loss of consciousness or sensory perception. There are two basic classes of analgesics: anti-inflammatory, routinely prescribed for short-term pain relief and for modest pain, and opioids used for either short-term or long term pain relief of severe pain. The anti-inflammatory analgesics generally provide analgesia, anti-inflammation, and antipyretic action. It has been reported that the mechanism of action may be to provide inhibition of the synthesis of prostaglandins. W. W. Douglas, "Polypeptides—angiotensin, plasma kinins, and other vasoactive agents; prostaglandins," *The Pharmacological Basis of Therapeutics*, 9th edition, L. S. Goodman and A. Gilman (eds.), MacMillan Publishing Co., Inc., New York, 1975. Prolonged use of anti-inflammatory analgesics have been known to cause gastrointestinal problems.

The opioid analgesics, or narcotics, include all natural or synthetic chemical compounds closely related to morphine and are thought to activate one or more receptors on brain neurons. Opioid analgesics have serious side effects and thus are used with discrimination. These side effects include: 1) tolerance, which requires gradually increasing doses to maintain analgesia; 2) physical dependence, which means that the narcotics must be withdrawn gradually if they are discontinued after prolonged use; 3) constipation, which requires careful attention to bowel function, including use of stool softeners, laxatives, and enemas; and 4) various degrees of somnolence, or drowsiness, which requires adjustments in dosages and dose scheduling, or possibly varying the type of narcotic to find one better tolerated by the patient.

It has been reported that various treatments for pain are additive and should be used together rather than separately. For example, the combination of aspirin or acetaminophen and codeine is often prescribed to provide pain relief stronger than codeine by itself. Certain antidepressants prescribed for depression have been recommended as an analgesic adjuvant.

While pain management has been a problem faced by physicians for many years, available pain medications have ameliorated, but not alleviated the problem of pain treatment. A significant problem remains in that detrimental side effects are often caused by pain-relieving medications as detailed above. Thus, there remains a continuing need for alternative pain therapy regimens which would address the need for pain reduction but also reduce these side effects.

Surprisingly, it has now been discovered that N-L-α-aspartyl-L-phenylalanine 1-methyl ester and derivatives have analgesic properties, relieving pain and restoring function of soft tissues, muscles, ligaments, tendons, bones, and joints. Further, when taken in combination with other analgesic agents, N-L-α-aspartyl-L-phenylalanine 1-methyl ester provides an additive analgesic effect. The detrimental side effects inherent in pain therapy known to the art can be reduced through the use of N-L-α-aspartyl-L-phenylalanine 1-methyl ester in pain therapy and management.

SUMMARY OF THE INVENTION

In one aspect of the invention, N-L-α-aspartyl-L-phenylalanine 1-methyl ester or its derivatives or both are used in a method for decreasing pain in a human patient.

In another aspect, N-L-α-aspartyl-L-phenylalanine 1-methyl ester or its derivatives or both are used in combination with an anti-inflammatory analgesic drug of other composition in a pain treatment regimen.

In another aspect, N-L-α-aspartyl-L-phenylalanine 1-methyl ester or its derivatives or both are used in combination with an opioid analgesic in a pain treatment regimen.

In yet another aspect, N-L-α-aspartyl-L-phenylalanine 1-methyl ester or its derivatives or both are used in treating osteoarthritis.

Another aspect of the invention concerns pharmaceutical dosage form containing N-L-α-aspartyl-L-phenylalanine 1-methyl ester or its derivatives or both.

DETAILED DESCRIPTION

Figure 1:
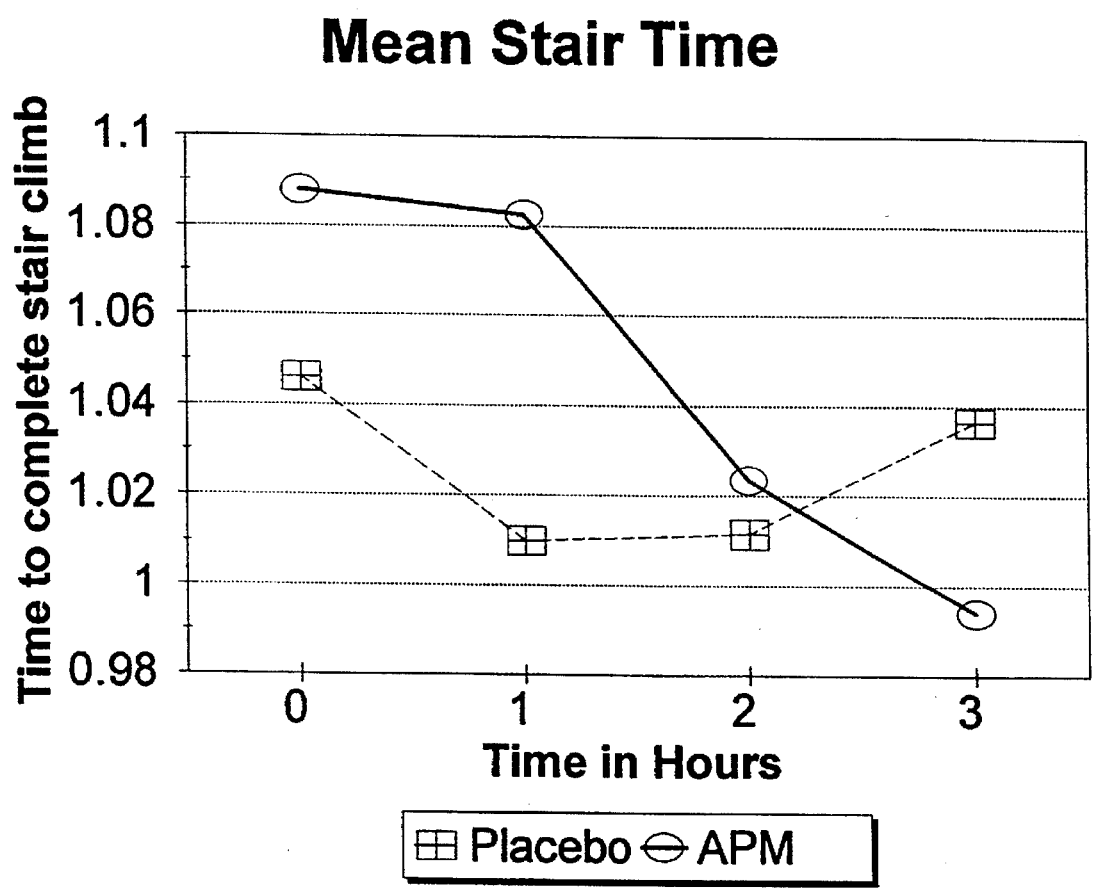
FIG. 1 is a graph depicting the average time required to ascend and descend stairs for the APM and control treatment groups measured over time.

Chronic pain has been shown to be associated with various pathological conditions such as osteoarthritis, inflammation, multiple sclerosis, and myocardial infarction. It has now been found that N-L-α-aspartyl-L-phenylalanine 1-methyl ester (APM), which has been sold under the trade name of ASPARTAME™ (G. D. Searle & Company, Chicago, Ill.) and its derivatives offer medicinal qualities beneficial in the treatment of chronic pain. One can use an effective amount of APM to effect a reduction in perceived pain by the recipient within one hour of dosage. The effective amount per dosage is about 40 milligrams to about 540 milligrams. An effective amount of APM which can effect pain relief after one dose is from about 80 milligrams to about 320 milligrams. A preferred range is from about 80 milligrams to about 160 milligrams. Most preferred is about 160 milligrams. The dosage can be repeated over time for continued relief, preferably at 160 milligrams every 4 hours. APM can also be administered together with other analgesics such as acetaminophen, phenacetin, aspirin, ibuprofen, phenylbutazone, indomethacin and derivatives, opiates and derivatives, piroxacam, and steroidal and nonsteroidal anti-inflammatory agents, providing additive analgesic properties.

APM can be administered orally, parenterally, intraperitoneally, or sublingually. It can be administered via ingestion of a food substance containing APM in a volume sufficient to achieve therapeutic levels. Alternatively, it can be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose; an integrating agent such as alginic acid, corn starch; a lubricant such as magnesium stearate; a glidant such as colloidal silicon dioxide; and additional sweetening and flavoring agents. When a capsule form is used the liquid carrier such as a fatty oil may be used. Capsules and tablets can be coated with sugar, shellac and other enteric agents as is known. APM can also be in a controlled-release formulation.

APM is available commercially. Its preparation is also disclosed in U.S. Pat. No. 3,492,131. It is believed that various modifications can be made to the APM molecule and the resulting derivatives will also have utility in the claimed invention. Since the 1-methyl ester portion of the molecule is not believed to contribute to the analgesic activity of the molecule, N-L-α-aspartyl-L-phenylalanine itself or other lower alkyl esters are believed to be effective. Other possible analgesic physiologically acceptable derivatives are believed to include N-acyl-L-(beta-substituted)-aspartyl-L-phenylalanine lower alkyl esters and N-acyl-L-(beta-substituted)-aspartyl-L-phenylalanine. Chemical modifications made to the APM molecule which do not reduce the analgesic physiologically active properties disclosed herein thus fall within the scope of this invention.

EXAMPLE 1

Osteoarthritis

In a well-controlled double-blind crossover study, patients suffering from osteoarthritis were given the tasks of climbing stairs, walking, and hand gripping, all of which are known to cause chronic pain in osteoarthritic patients, following treatment with either APM or a placebo. The study was performed twice for all patients, and prior to each study, all other analgesics were withheld for twenty-four hours. During the first study, one test group of eleven patients were randomly administered 4 tablets of either aspartame (76 milligrams; 19 milligrams/tablet) or placebo, and another test group of nine patients were randomly given 8 tablets of either aspartame (152 milligrams; 19 milligrams/tablet) or placebo. During the second study, each patient was given the same number of tablets but were given the opposite medication from what they had received in the first study. Following each test, data analysis of the recovered information was completed using non-parametric analyses of variance and distribution free assessments of the measured variable.

Stair Climbing

Twenty osteoarthritic patients divided into groups of nine and eleven each were asked to ascend and descend one flight of stairs, making a total of three trips with one-hour rest periods between trips. Right after the first baseline trip, patients were administered the test medication. All patients then made three subsequent trips up and down the stairs. Table I and FIG. 1 present an objective measurement of performance with respect to the time required for each patient to ascend and descend one flight of stairs. The mean results show that over time the 4-tablet APM group decreased the stair time, with a 9.6% decrease for the last trip. For the 8-tablet APM group, a decrease of 11.9% was observed for the second trip after dosing and 6.9% for the last trip. After administration of the placebo, the 4-tablet placebo group showed a decrease in stair time of 6.5% for the first and second trips after dosing, and 3.7% for the last trip. The 8-tablet placebo group showed a gradual increase in stair time with a maximum increase of 2% for the last trip.

A subjective measurement of stair pain was made by administering a visual analog pain assessment to the patients. A baseline assessment for various joints, usually three joints, was taken one hour prior to the first baseline trip, and the assessment was then repeated for each of the four trips. Each patient made an assessment under a nurse's supervision (same nurse throughout study) as to the amount of pain involved on

TABLE I

Stair Time with and without APM

| Subject # | Stair Climb Time (min) Hours after Treatment | | | |
|---|---|---|---|---|
| | 0 | 1 | 2 | 3 |
| Control group - 4 tablets placebo | | | | |
| 1 | 1.04 | 0.59 | 0.59 | 1.01 |
| 2 | 0.92 | 0.99 | 0.97 | 0.96 |
| 3 | 1.19 | 1.12 | 1.10 | 1.15 |
| 4 | 1.00 | 1.03 | 1.04 | 1.04 |
| 5 | 0.90 | 0.91 | 0.94 | 0.98 |
| 6 | 2.09 | 1.50 | 1.51 | 1.56 |
| 7 | 0.79 | 0.79 | 0.80 | 0.81 |
| 8 | 1.28 | 1.27 | 1.23 | 1.24 |
| 9 | 1.25 | 1.26 | 1.26 | 1.26 |
| 10 | 0.72 | 1.02 | 1.01 | 0.80 |
| 11 | 0.56 | 0.58 | 0.54 | 0.55 |
| mean | 1.07 | 1.00 | 1.00 | 1.03 |
| APM group - 4 tablets APM | | | | |
| 1 | 1.05 | 1.01 | 1.00 | 1.01 |
| 2 | 0.96 | 0.96 | 0.93 | 0.88 |
| 3 | 1.10 | 1.08 | 1.04 | 1.02 |

TABLE I-continued

Stair Time with and without APM

Figure 2:
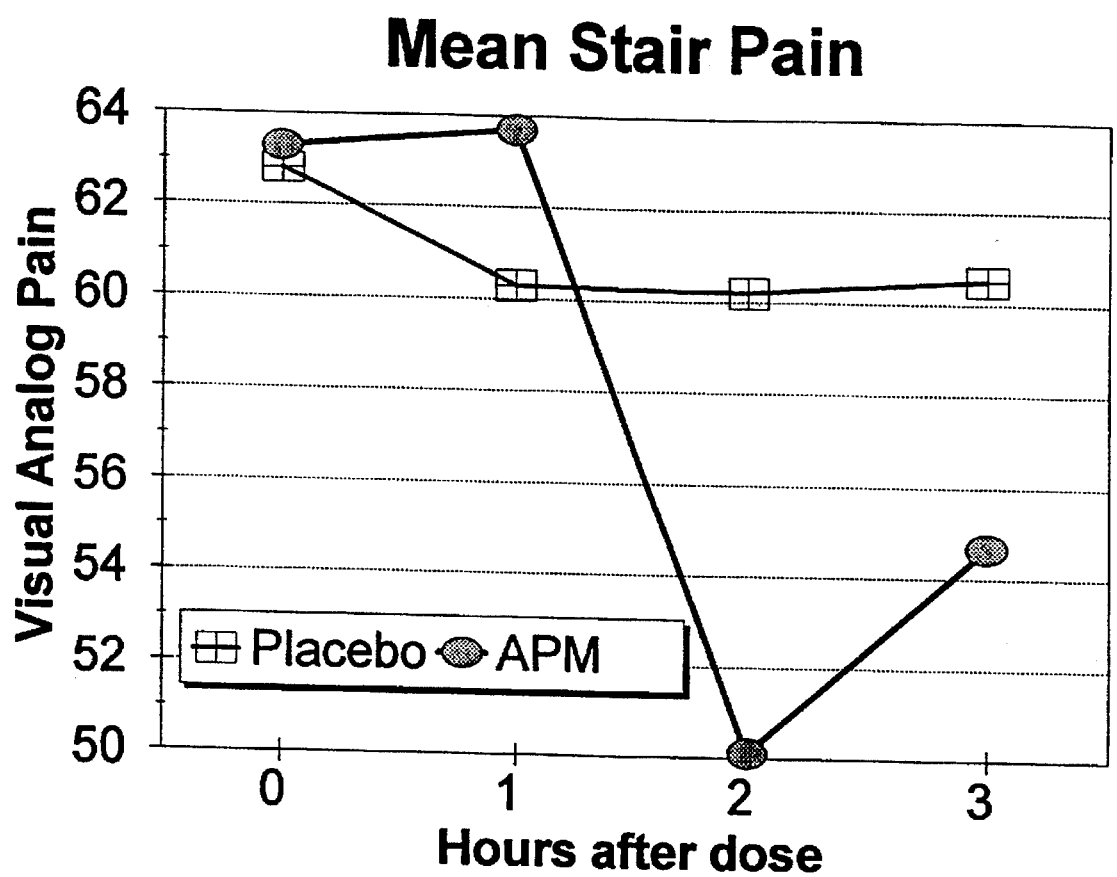
FIG. 2 is a graph depicting the average pain experienced by the APM and control treatment groups upon ascending and descending stairs measured over time.

| Subject # | Stair Climb Time (min) Hours after Treatment | | | |
|---|---|---|---|---|
| | 0 | 1 | 2 | 3 |
| 4 | 1.10 | 1.10 | 1.07 | 1.06 |
| 5 | 0.90 | 0.91 | 0.89 | 0.92 |
| 6 | 2.07 | 2.10 | 2.16 | 1.54 |
| 7 | 0.78 | 0.79 | 0.79 | 0.78 |
| 8 | 1.36 | 1.30 | 1.28 | 1.33 |
| 9 | 1.23 | 1.25 | 1.24 | 1.25 |
| 10 | 1.01 | 1.02 | 1.02 | 1.02 |
| 11 | 1.07 | 1.03 | 1.01 | 0.59 |
| mean | 1.15 | 1.14 | 1.13 | 1.04 |
| Control group - 8 tablets placebo | | | | |
| 12 | 0.94 | 0.94 | 0.91 | 0.93 |
| 13 | 0.90 | 0.92 | 0.90 | 0.96 |
| 14 | 1.44 | 1.43 | 1.51 | 1.56 |
| 15 | 0.49 | 0.51 | 0.54 | 0.58 |
| 16 | 1.24 | 1.25 | 1.25 | 1.22 |
| 17 | 1.07 | 1.07 | 1.13 | 1.13 |
| 18 | 1.14 | 1.11 | 1.09 | 1.10 |
| 19 | 0.81 | 0.84 | 0.83 | 0.84 |
| 20 | 1.15 | 1.08 | 1.08 | 1.05 |
| mean | 1.02 | 1.02 | 1.03 | 1.04 |
| APM group - 8 tablets APM | | | | |
| 12 | 0.94 | 0.92 | 0.89 | 0.86 |
| 13 | 0.87 | 0.88 | 0.89 | 0.90 |
| 14 | 1.45 | 1.42 | 1.35 | 1.44 |
| 15 | 0.50 | 0.55 | 0.56 | 0.51 |
| 16 | 1.33 | 1.25 | 1.27 | 1.25 |
| 17 | 1.00 | 1.03 | 0.55 | 0.59 |
| 18 | 1.14 | 1.16 | 1.08 | 1.08 |
| 19 | 0.84 | 0.88 | 0.86 | 0.83 |
| 20 | 1.06 | 1.02 | 0.58 | 1.00 |
| mean | 1.01 | 1.01 | 0.89 | 0.94 |
| Total mean score by treatment group | | | | |
| Control | 1.05 | 1.01 | 1.01 | 1.04 |
| APM | 1.09 | 1.08 | 1.02 | 0.99 | a scale marked with increments for none, a little, more, a lot, and most. A numerical conversion of the marks on the scale in millimeters taken as the distance from the absence of pain mark were made. The representation of this assessment scale where the lower the number the lesser the pain, and the higher the number, the greater the pain is given in Table II and FIG. 2 as an average value for all rated joints. Referring to the mean, there was a marked decrease in the amount of pain associated with ascending and descending stairs in the APM groups in comparison to that in the placebo groups. The 4-tablet placebo group showed increased pain over the pre-climbing baseline assessment for each trip; however, while the 4-tablet APM group also experienced increased pain over the pre-climbing baseline assessment for the first two trips, they had decreased pain below or just above the pre-climbing baseline assessment for the last two trips.

Table III provides pain assessment measurements for the most sensitive joint for some of the patients taken at one hour and two hours after treatment. For the 4-tablet treatment groups, the placebo group showed a slight increase in pain (2.2%), while the APM group experienced a 52.2% decrease in pain. The 8-tablet APM group also experienced a significant decrease in pain (48.2%), compared to a 24.5% decrease in pain for the 8-tablet placebo group.

Figure 3:
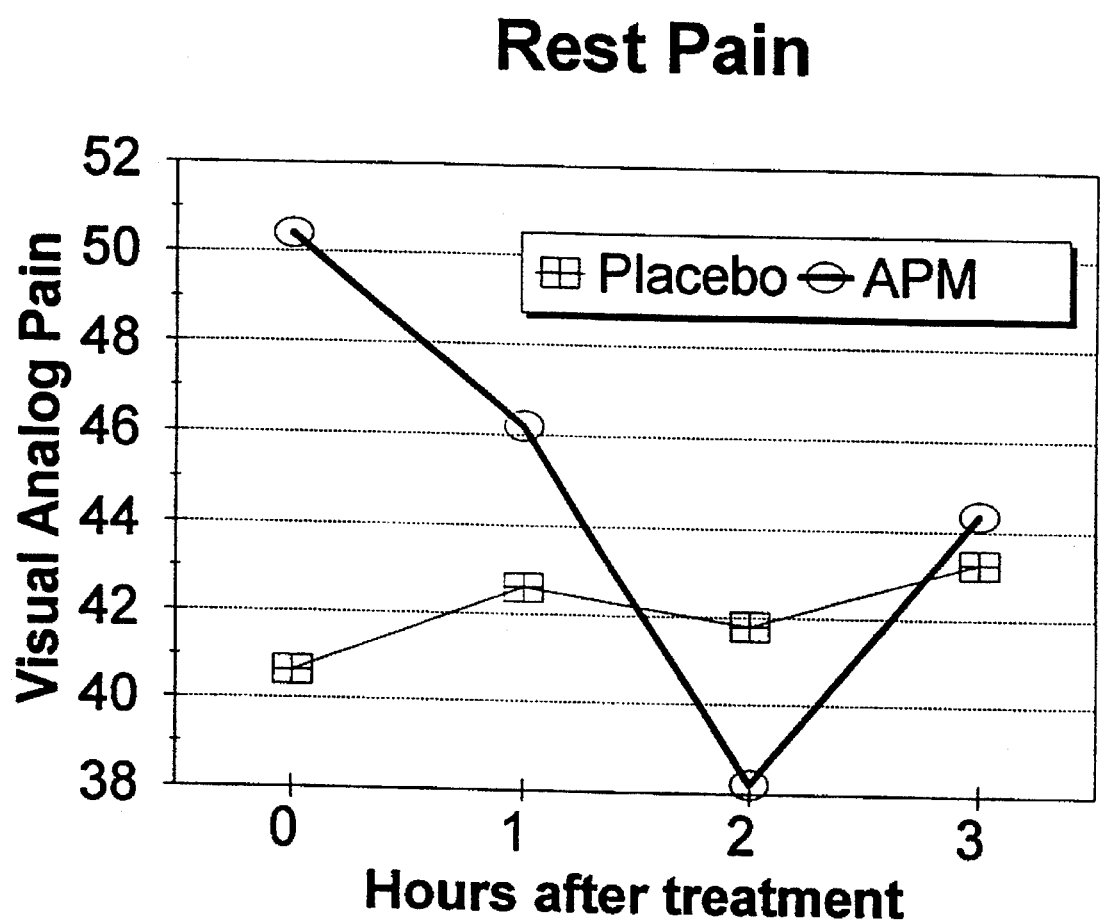
FIG. 3 is a graph depicting the average rest pain experienced by the APM and control treatment groups taken after a one hour rest period following ascending and descending stairs measured over time.

An evaluation of pain was also measured using the visual analog pain assessment method by the patient at the end of each rest period (Table IV and FIG. 3).

TABLE II

Stair Pain with and without APM

Stair Pain (relative numerical scale)
Hours after Treatment

| Subject # | −1 | 0 | 1 | 2 | 3 |
|---|---|---|---|---|---|
| *Control group - 4 tablets placebo* | | | | | |
| 1 | 27 | 24 | 33 | 42 | 36 |
| 2 | 62 | 102 | 119 | 91 | 74 |
| 3 | 51 | 85 | 67 | 110 | 73 |
| 4 | 31 | 73 | 25 | 32 | 31 |
| 5 | 42 | 59 | 38 | 73 | 58 |
| 6 | 93 | 117 | 118 | 126 | 127 |
| 7 | 24 | 81 | 97 | 89 | 88 |
| 8 | 41 | 22 | 31 | 28 | 21 |
| 9 | 31 | 46 | 64 | 45 | 75 |
| 10 | 55 | 72 | 78 | 88 | 85 |
| 11 | 36 | 48 | 50 | 31 | 36 |
| mean | 44.82 | 68.55 | 65.45 | 68.64 | 64.00 |
| *APM group - 4 tablets APM* | | | | | |
| 1 | 45 | 47 | 48 | 36 | 22 |
| 2 | 24 | 80 | 91 | 32 | 38 |
| 3 | 106 | 130 | 130 | 73 | 73 |
| 4 | 79 | 63 | 70 | 40 | 42 |
| 5 | 41 | 71 | 56 | 56 | 44 |
| 6 | 46 | 95 | 130 | 101 | 130 |
| 7 | 28 | 87 | 87 | 56 | 74 |
| 8 | 59 | 28 | 30 | 28 | 62 |
| 9 | 94 | 56 | 47 | 30 | 30 |
| 10 | 67 | 83 | 96 | 91 | 105 |
| 11 | 36 | 45 | 49 | 52 | 24 |
| mean | 56.82 | 71.36 | 75.82 | 54.09 | 58.55 |
| *Control group - 8 tablets placebo* | | | | | |
| 12 | 33 | 66 | 60 | 51 | 59 |
| 13 | 22 | 40 | 26 | 30 | 24 |
| 14 | 35 | 74 | 115 | 116 | 118 |
| 15 | 45 | 74 | 21 | 33 | 50 |
| 16 | 50 | 52 | 50 | 51 | 56 |
| 17 | 22 | 28 | 26 | 22 | 21 |
| 18 | 62 | 74 | 92 | 77 | 74 |
| 19 | 8 | 49 | 63 | 49 | 83 |
| 20 | 43 | 45 | 33 | 20 | 21 |
| mean | 35.56 | 55.78 | 54.00 | 49.89 | 56.22 |
| *APM group - 8 tablets APM* | | | | | |
| 12 | 42 | 72 | 71 | 51 | 53 |
| 13 | 31 | 31 | 39 | 31 | 31 |
| 14 | 69 | 97 | 84 | 85 | 117 |
| 15 | 33 | 35 | 23 | 31 | 33 |
| 16 | 53 | 52 | 54 | 53 | 54 |
| 17 | 39 | 31 | 15 | 21 | 17 |
| 18 | 25 | 48 | 65 | 49 | 56 |
| 19 | 57 | 78 | 63 | 72 | 74 |
| 20 | 34 | 37 | 26 | 14 | 14 |
| mean | 42.56 | 53.44 | 48.89 | 45.22 | 49.89 |
| *Total mean score by treatment group* | | | | | |
| Control | 40.65 | 62.80 | 60.30 | 60.20 | 60.50 |
| APM | 50.40 | 63.30 | 63.70 | 50.10 | 54.65 |

TABLE III

Stair Pain of Most Sensitive Joint with and without APM

Stair Pain (relative numerical scale)
Hours after Treatment

| Subject # | 1 | 2 |
|---|---|---|
| *Control group - 4 tablets placebo* | | |
| 1 | 24 | 43 |
| 2 | 113 | 105 |
| 3 | 63 | 92 |
| 4 | 25 | 32 |
| 5 | 21 | 57 |
| 6 | 149 | 149 |
| 7 | 97 | 77 |
| 8 | 16 | 21 |
| 9 | 73 | 35 |
| 10 | — | — |
| 11 | 33 | 17 |
| mean | 61.40 | 62.80 |
| *APM group - 4 tablets APM* | | |
| 1 | 53 | 35 |
| 2 | 107 | 53 |
| 3 | 130 | 16 |
| 4 | 104 | 46 |
| 5 | 56 | 22 |
| 6 | 150 | 106 |
| 7 | 75 | 39 |
| 8 | 45 | 26 |
| 9 | 73 | 37 |
| 10 | — | — |
| 11 | 32 | 14 |
| mean | 82.50 | 39.40 |
| *Control group - 8 tablets placebo* | | |
| 12 | 48 | 39 |
| 13 | 26 | 38 |
| 14 | — | — |
| 15 | — | — |
| 16 | — | — |
| 17 | — | — |
| 18 | 129 | 93 |
| 19 | 86 | 58 |
| 20 | 33 | 15 |
| mean | 64.40 | 48.60 |
| *APM group - 8 tablets APM* | | |
| 12 | 71 | 11 |
| 13 | 55 | 39 |
| 14 | — | — |
| 15 | — | — |
| 16 | — | — |
| 17 | — | — |
| 18 | 32 | 15 |
| 19 | 86 | 72 |
| 20 | 36 | 8 |
| mean | 56.00 | 29.00 |
| *Total mean score by treatment group* | | |
| Control | 62.40 | 58.07 |
| APM | 73.67 | 35.93 |

TABLE IV

Rest Pain with and without APM

Rest Pain (relative numerical scale)
Hours after Treatment

| Subject # | 0 | 1 | 2 | 3 |
|---|---|---|---|---|
| *Control group - 4 tablets placebo* | | | | |
| 1 | 27 | 31 | 32 | 45 |
| 2 | 62 | 79 | 36 | 48 |
| 3 | 51 | 10 | 30 | 15 |
| 4 | 31 | 46 | 30 | 30 |
| 5 | 42 | 54 | 40 | 41 |
| 6 | 93 | 116 | 127 | 129 |
| 7 | 24 | 39 | 42 | 40 |
| 8 | 41 | 35 | 23 | 16 |
| 9 | 31 | 31 | 48 | 58 |
| 10 | 55 | 70 | 73 | 80 |
| 11 | 36 | 35 | 32 | 25 |
| mean | 44.82 | 49.64 | 46.64 | 47.91 |
| *APM group - 4 tablets APM* | | | | |
| 1 | 45 | 37 | 45 | 17 |
| 2 | 24 | 50 | 77 | 78 |
| 3 | 106 | 25 | 14 | 30 |
| 4 | 79 | 68 | 56 | 40 |
| 5 | 41 | 40 | 39 | 41 |
| 6 | 46 | 77 | 94 | 99 |
| 7 | 28 | 9 | 8 | 39 |
| 8 | 59 | 49 | 25 | 27 |
| 9 | 94 | 77 | 32 | 24 |
| 10 | 67 | 80 | 89 | 96 |
| 11 | 36 | 38 | 43 | 69 |
| mean | 56.82 | 50.00 | 47.45 | 50.91 |
| *Control group - 8 tablets placebo* | | | | |
| 12 | 33 | 34 | 16 | 14 |
| 13 | 22 | 24 | 28 | 32 |
| 14 | 35 | 78 | 115 | 118 |
| 15 | 45 | 19 | 32 | 32 |
| 16 | 50 | 53 | 50 | 50 |
| 17 | 22 | 19 | 18 | 24 |
| 18 | 62 | 35 | 30 | 34 |
| 19 | 8 | 8 | 8 | 10 |
| 20 | 43 | 36 | 26 | 24 |
| mean | 35.56 | 34.00 | 35.89 | 37.56 |
| *APM group - 8 tablets APM* | | | | |
| 12 | 42 | 58 | 32 | 38 |
| 13 | 31 | 32 | 28 | 33 |
| 14 | 69 | 73 | 53 | 86 |
| 15 | 33 | 20 | 19 | 27 |
| 16 | 53 | 54 | 52 | 52 |
| 17 | 39 | 35 | 20 | 16 |
| 18 | 25 | 33 | 12 | 20 |
| 19 | 57 | 39 | 9 | 39 |
| 20 | 34 | 30 | 17 | 16 |
| mean | 42.56 | 41.56 | 26.89 | 36.33 |
| *Total mean score by treatment group* | | | | |
| Control | 40.65 | 42.60 | 41.80 | 43.25 |
| APM | 50.40 | 46.20 | 38.20 | 44.35 |

Figure 4:
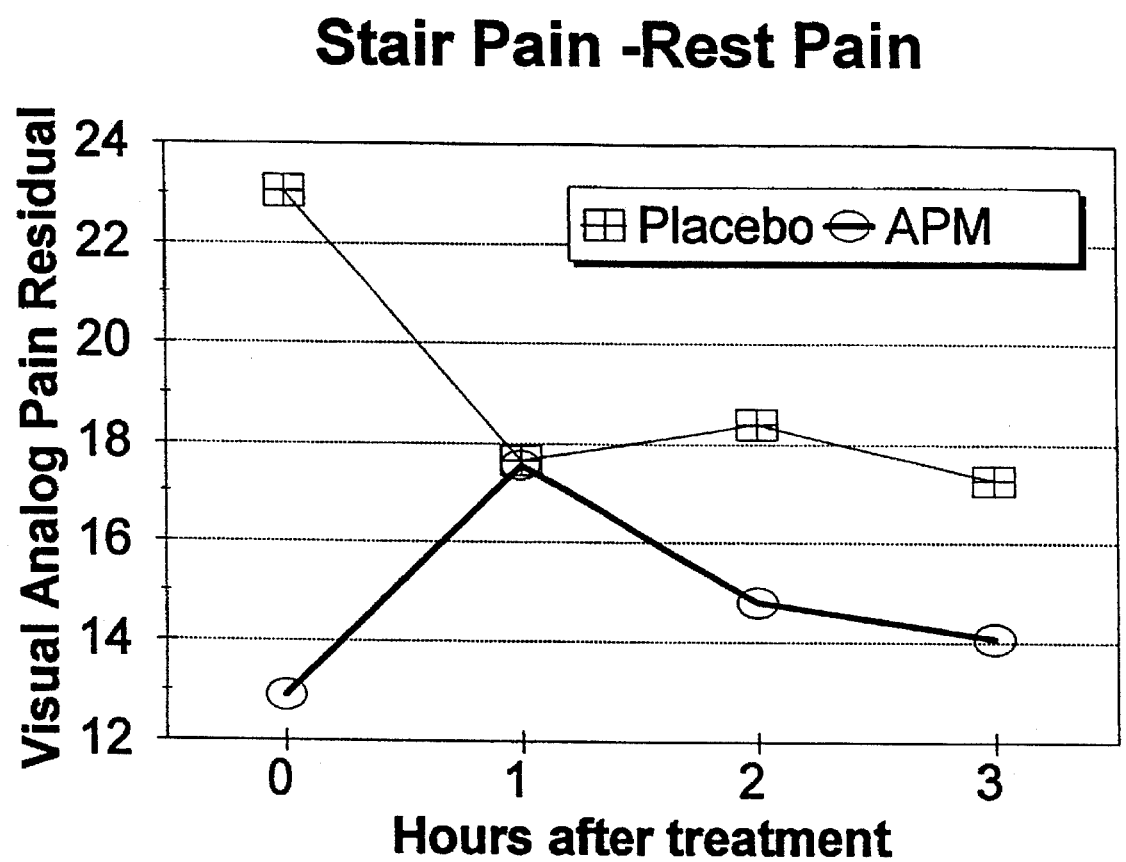
FIG. 4 is a graph depicting the difference between stair pain and rest pain experienced by the APM and control treatment groups upon ascending and descending stairs measured over time.

While the average rest pain generally increased for both placebo groups, the 4-tablet APM group experienced a 12.2%, 16.5%, and 10.4% decrease in rest pain from pre-treatment over time, while the 8-tablet APM group, a 2.3%, 36.8% and 14.6% decrease. In Table V and FIG. 4 the mean difference between stair pain and rest pain for each patient at each time period is given, showing that the mean difference of the APM groups was lower than the placebo groups. As indicated by the negative numbers, some patients in both groups experienced greater rest pain than stair climb pain.

Walking Distance

Figure 5:
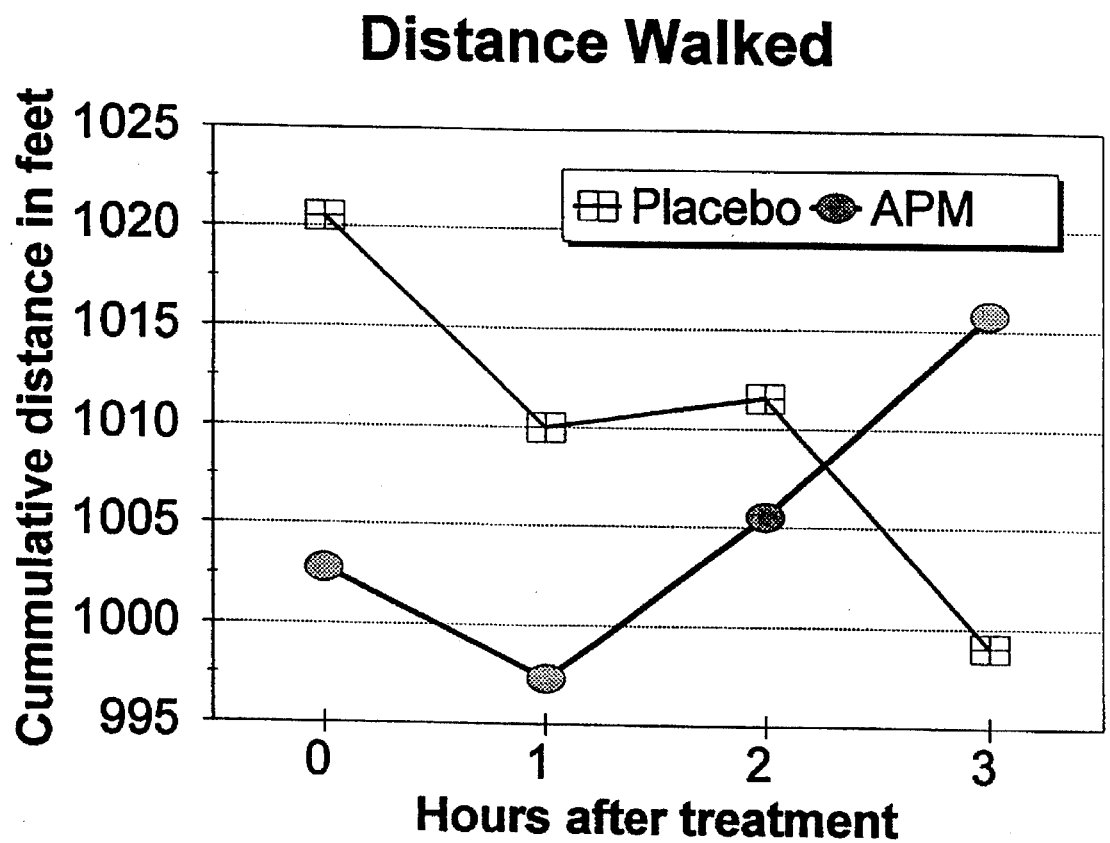
FIG. 5 is a graph depicting the average distance walked by the APM and control treatment groups measured over time.

Chronic pain was examined in respect to distance walking at a comfortable speed for a five minute period. A pre-walking baseline pain assessment was performed. After establishing a baseline walking distance, the 4- and 8-tablet APM groups were given 76 milligrams and 152 milligrams APM, respectively, while the 4- and 8-tablet control groups were given the appropriate number of placebo tablets. After resting for one hour, the patients repeated the 5-minute walking procedure three times with one hour rest periods between trips. Table VI and FIG. 5 show the total distance walked in terms of feet traveled. The average distance walked in the control groups decreased slightly over time, with the mean varying from −0.5% to −2.2% from baseline. Comparatively, the average distance walked in the APM groups varied from −0.4% to 1.8% from baseline. Although the average distance

TABLE V

Stair Pain v. Rest Pain with and without APM

Stair Pain Minus Rest Pain
Hours after Treatment

| Subject # | 0 | 1 | 2 | 3 |
|---|---|---|---|---|
| *Control groups - 4 or 8 tablets placebo* | | | | |
| 1 | 22 | 1 | 10 | −9 |
| 2 | 40 | 40 | 55 | 26 |
| 3 | 34 | 57 | 80 | 58 |
| 4 | 42 | −21 | 2 | 1 |
| 5 | 17 | −16 | 33 | 17 |
| 6 | 24 | 2 | −1 | −2 |
| 7 | 57 | 58 | 47 | 48 |
| 8 | −19 | −4 | 5 | 5 |
| 9 | 15 | 33 | −3 | 17 |
| 10 | 17 | 8 | 15 | 5 |
| 11 | 12 | 15 | −1 | 11 |
| 12 | 33 | 26 | 35 | 45 |
| 13 | 18 | 2 | 2 | −8 |
| 14 | 39 | 37 | 1 | 0 |
| 15 | 29 | 2 | 1 | 18 |
| 16 | 20 | −3 | 1 | 6 |
| 17 | 6 | 7 | 4 | −3 |
| 18 | 12 | 57 | 47 | 40 |
| 19 | 41 | 55 | 41 | 73 |
| 20 | 2 | −3 | −6 | −3 |
| mean | 23.05 | 17.65 | 18.40 | 17.25 |
| *APM groups - 4 or 8 tablets APM* | | | | |
| 1 | 2 | 11 | −9 | 5 |
| 2 | 56 | 41 | −45 | −40 |
| 3 | 24 | 105 | 59 | 43 |
| 4 | −16 | 2 | −16 | 2 |
| 5 | 30 | 16 | 17 | 3 |
| 6 | 49 | 53 | 7 | 31 |
| 7 | 59 | 78 | 48 | 35 |
| 8 | −31 | −19 | −2 | 35 |
| 9 | −38 | −30 | −2 | −4 |
| 10 | 16 | 16 | 2 | 9 |
| 11 | −9 | 11 | 9 | −45 |
| 12 | 30 | 13 | 19 | 15 |
| 13 | 0 | 7 | 3 | −2 |
| 14 | 28 | 11 | 84 | 116 |
| 15 | 2 | 3 | 12 | 6 |
| 16 | −1 | 0 | 1 | 2 |
| 17 | −8 | −20 | 1 | 1 |
| 18 | 23 | 32 | 37 | 36 |
| 19 | 21 | 25 | 74 | 35 |
| 20 | 3 | −4 | −3 | −2 |
| mean | 12.90 | 17.55 | 14.78 | 14.06 |

TABLE VI

Walking Distance with and without APM

Walking Distance (feet) Hours after Treatment

| Subject # | 0 | 1 | 2 | 3 |
|---|---|---|---|---|
| *Control group - 4 tablets placebo* | | | | |
| 1 | 1035 | 1040 | 1055 | 1045 |
| 2 | 895 | 875 | 895 | 825 |
| 3 | 1000 | 980 | 1030 | 1000 |
| 4 | 1010 | 980 | 970 | 990 |
| 5 | 1100 | 1095 | 1095 | 1120 |
| 6 | 800 | 775 | 810 | 800 |
| 7 | 1325 | 1295 | 1310 | 1295 |
| 8 | 865 | 900 | 920 | 890 |
| 9 | 840 | 865 | 850 | 810 |
| 10 | 1175 | 1110 | 1085 | 1100 |
| 11 | 1150 | 1125 | 1105 | 1100 |
| mean | 1017.73 | 1003.64 | 1011.36 | 997.73 |
| *APM group - 4 tablets APM* | | | | |
| 1 | 990 | 1000 | 1000 | 1000 |
| 2 | 880 | 840 | 835 | 870 |
| 3 | 1025 | 1080 | 1090 | 1100 |
| 4 | 910 | 885 | 900 | 910 |
| 5 | 1075 | 1075 | 1070 | 1060 |
| 6 | 755 | 770 | 785 | 810 |
| 7 | 1320 | 1320 | 1325 | 1310 |
| 8 | 820 | 825 | 890 | 885 |
| 9 | 830 | 810 | 850 | 880 |
| 10 | 1300 | 1235 | 1245 | 1220 |
| 11 | 1010 | 1000 | 1025 | 1070 |
| mean | 992.27 | 985.45 | 1001.36 | 1010.45 |
| *Control group - 8 tablets placebo* | | | | |
| 12 | 935 | 930 | 920 | 910 |
| 13 | 1150 | 1160 | 1145 | 1120 |
| 14 | 780 | 785 | 760 | 770 |
| 15 | 1230 | 1250 | 1240 | 1170 |
| 16 | 900 | 930 | 940 | 920 |
| 17 | 1065 | 1025 | 995 | 1000 |
| 18 | 1095 | 1070 | 1085 | 1120 |
| 19 | 1350 | 1305 | 1300 | 1260 |
| 20 | 710 | 705 | 720 | 735 |
| mean | 1023.89 | 1017.78 | 1011.67 | 1000.56 |
| *APM group - 8 tablets APM* | | | | |
| 12 | 980 | 930 | 910 | 1000 |
| 13 | 1120 | 1140 | 1115 | 1120 |
| 14 | 790 | 795 | 825 | 740 |
| 15 | 1210 | 1270 | 1260 | 1260 |
| 16 | 890 | 900 | 925 | 905 |
| 17 | 1000 | 995 | 960 | 1045 |
| 18 | 1075 | 1060 | 1070 | 1100 |
| 19 | 1285 | 1250 | 1250 | 1250 |
| 20 | 790 | 765 | 780 | 780 |
| mean | 1015.56 | 1011.67 | 1010.56 | 1022.22 |
| *Total mean score by treatment group* | | | | |
| Control | 1020.50 | 1010.00 | 1011.50 | 999.00 |
| APM | 1002.75 | 997.25 | 1005.50 | 1015.75 | walked decreased at one hour from baseline, there was an increase at 3 hours from baseline for both APM groups.

Figure 6:
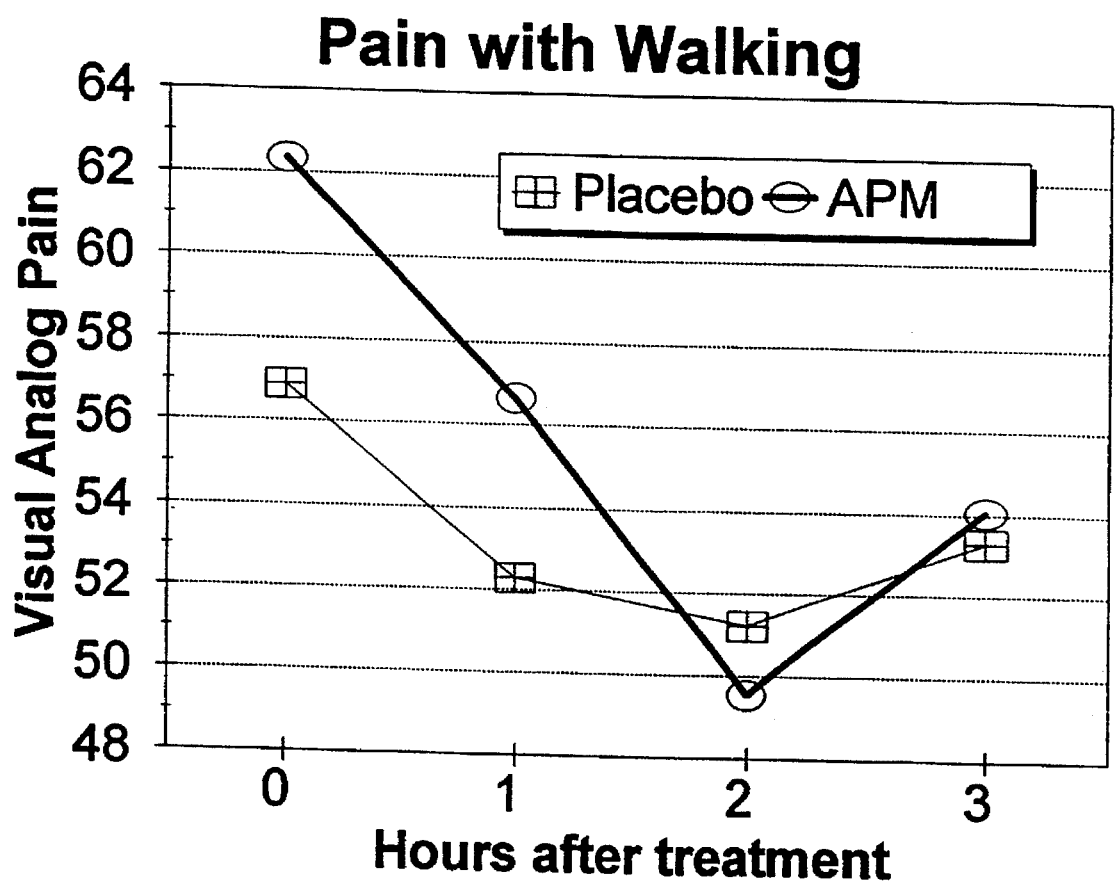
FIG. 6 is a graph depicting the average pain experienced by the APM and control treatment groups upon walking for five minutes measured over time.

Walking distance pain was recorded via the visual analog pain assessment. A baseline assessment was taken one hour prior to the first baseline trip. The assessment was then repeated for each of the four trips. A relative numerical representation of this assessment scale where the lower the number the lesser the pain, and the higher the number, the greater the pain is given in Table VII and FIG. 6. The average distance pain after the four walks increased over the pre-walking baseline assessment by 22.7 to 42.8% for the 4-tablet control group, and 20.6% to 35.6% for the 8-tablet control group. Comparatively, the patients in the 4-tablet APM group showed an increase in average distance pain after the baseline walk (23.0%) and the first walk after dosing (21.8%), while the average distance pain decreased below the pre-walking baseline assessment by 1.1% after the second walk after dosing and then increased to 11.4% above the pre-walking baseline assessment after the last walk. For the 8-tablet APM group, the average distance pain after the baseline walk increased over the pre-walking assessment by 24.8%; however, the average distance pain for the remaining three walks was right at or below the pre-walking baseline assessment.

TABLE VII

Walking Pain with and without APM

Walking Pain (relative numerical scale) Hours after Treatment

| Subject # | −1 | 0 | 1 | 2 | 3 |
|---|---|---|---|---|---|
| *Control group - 4 tablets placebo* | | | | | |
| 1 | 27 | 43 | 49 | 43 | 37 |
| 2 | 62 | 81 | 80 | 53 | 53 |
| 3 | 51 | 83 | 25 | 16 | 53 |
| 4 | 31 | 46 | 38 | 22 | 22 |
| 5 | 42 | 87 | 87 | 71 | 39 |
| 6 | 93 | 95 | 116 | 128 | 128 |
| 7 | 24 | 57 | 57 | 77 | 76 |
| 8 | 41 | 63 | 43 | 35 | 56 |
| 9 | 31 | 39 | 57 | 56 | 65 |
| 10 | 55 | 70 | 70 | 70 | 73 |
| 11 | 36 | 40 | 38 | 34 | 33 |
| mean | 44.82 | 64.00 | 60.00 | 55.00 | 57.73 |
| *APM group - 4 tablets APM* | | | | | |
| 1 | 45 | 60 | 53 | 33 | 35 |
| 2 | 24 | 50 | 62 | 42 | 99 |
| 3 | 106 | 118 | 94 | 32 | 13 |
| 4 | 79 | 51 | 63 | 54 | 59 |
| 5 | 41 | 71 | 71 | 73 | 74 |
| 6 | 46 | 81 | 93 | 100 | 100 |
| 7 | 28 | 58 | 40 | 37 | 42 |
| 8 | 59 | 71 | 86 | 65 | 85 |
| 9 | 94 | 83 | 49 | 29 | 30 |
| 10 | 67 | 74 | 86 | 90 | 100 |
| 11 | 36 | 52 | 64 | 63 | 59 |
| mean | 56.82 | 69.91 | 69.18 | 56.18 | 63.27 |
| *Control group - 8 tablets placebo* | | | | | |
| 12 | 33 | 68 | 17 | 21 | 18 |
| 13 | 22 | 29 | 43 | 57 | 47 |
| 14 | 35 | 55 | 95 | 114 | 114 |
| 15 | 45 | 75 | 32 | 49 | 55 |
| 16 | 50 | 51 | 60 | 61 | 72 |
| 17 | 22 | 26 | 27 | 30 | 28 |
| 18 | 62 | 87 | 52 | 59 | 42 |
| 19 | 8 | 8 | 41 | 8 | 38 |
| 20 | 43 | 35 | 19 | 20 | 17 |
| mean | 35.56 | 48.22 | 42.89 | 46.56 | 47.89 |
| *APM group - 8 tablets APM* | | | | | |
| 12 | 42 | 41 | 30 | 40 | 40 |
| 13 | 31 | 47 | 48 | 47 | 46 |
| 14 | 69 | 95 | 84 | 84 | 96 |
| 15 | 33 | 38 | 31 | 36 | 27 |
| 16 | 53 | 54 | 61 | 54 | 56 |
| 17 | 39 | 35 | 28 | 27 | 24 |
| 18 | 25 | 49 | 55 | 29 | 44 |
| 19 | 57 | 75 | 11 | 40 | 39 |
| 20 | 34 | 44 | 24 | 16 | 13 |
| mean | 42.56 | 53.11 | 41.33 | 41.44 | 42.78 |
| *Total mean score by treatment group* | | | | | |
| Control | 40.65 | 56.90 | 52.30 | 51.20 | 53.30 |
| APM | 50.40 | 62.35 | 56.65 | 49.55 | 54.05 |

Grip Strength

Figure 7:
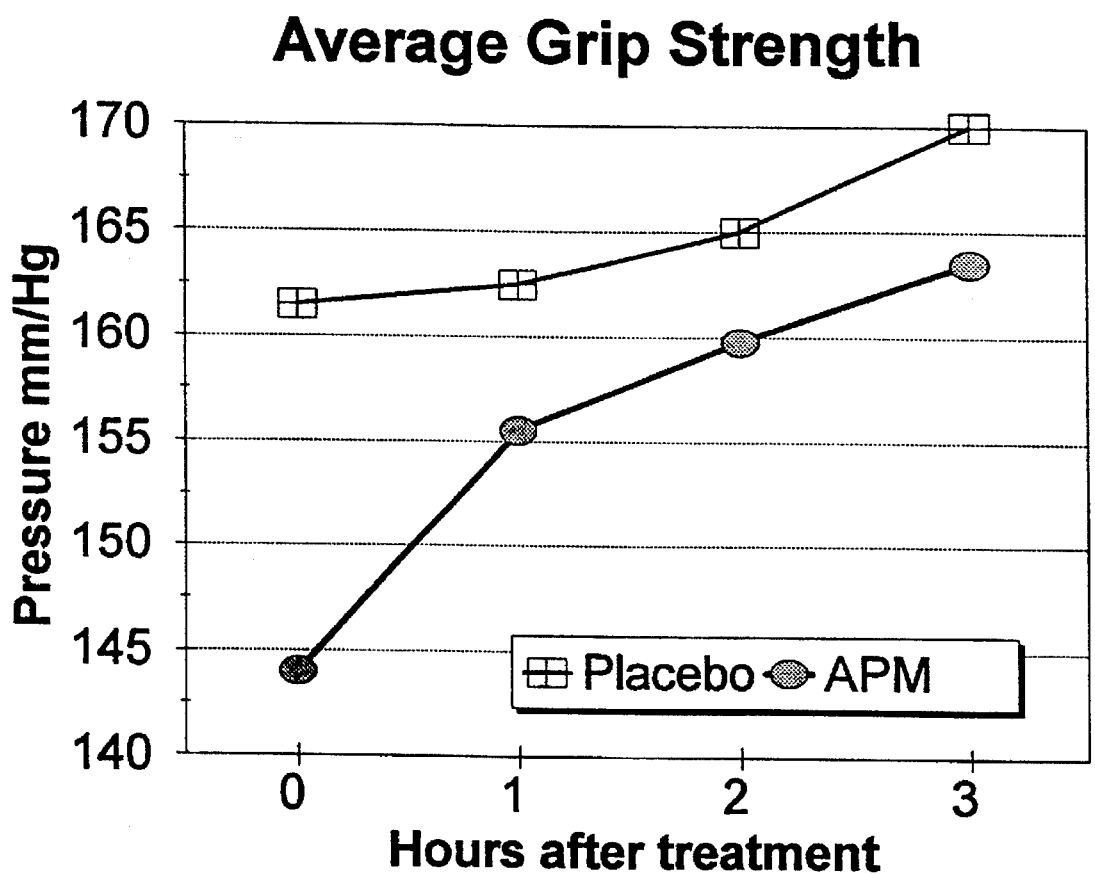
FIG. 7 is a graph depicting the average grip strength for the APM and control treatment groups measured over time.

Grip strength was measured by placing the cuff into a cloth bag and filling with air to a resting pressure of 20 mmHg for easy gripping. Each patient gripped the cloth bag, and the increase in pressure registered as change in mmHg on the cuff was recorded. Following a baseline gripping measurement, the 4- and 8-tablet APM groups were given 76 milligrams and 152 milligrams APM, respectively, while the 4- and 8-tablet control groups were given the appropriate number of placebo tablets. After a one hour rest period, the gripping measurement was repeated three more times with a one hour rest period between each measurement. As shown in Table VIII and FIG. 7, both APM groups and the 4-tablet control group basically showed increasing grip strength over time. The 8-tablet control varied about 2% to 3% above and below baseline.

Figure 8:
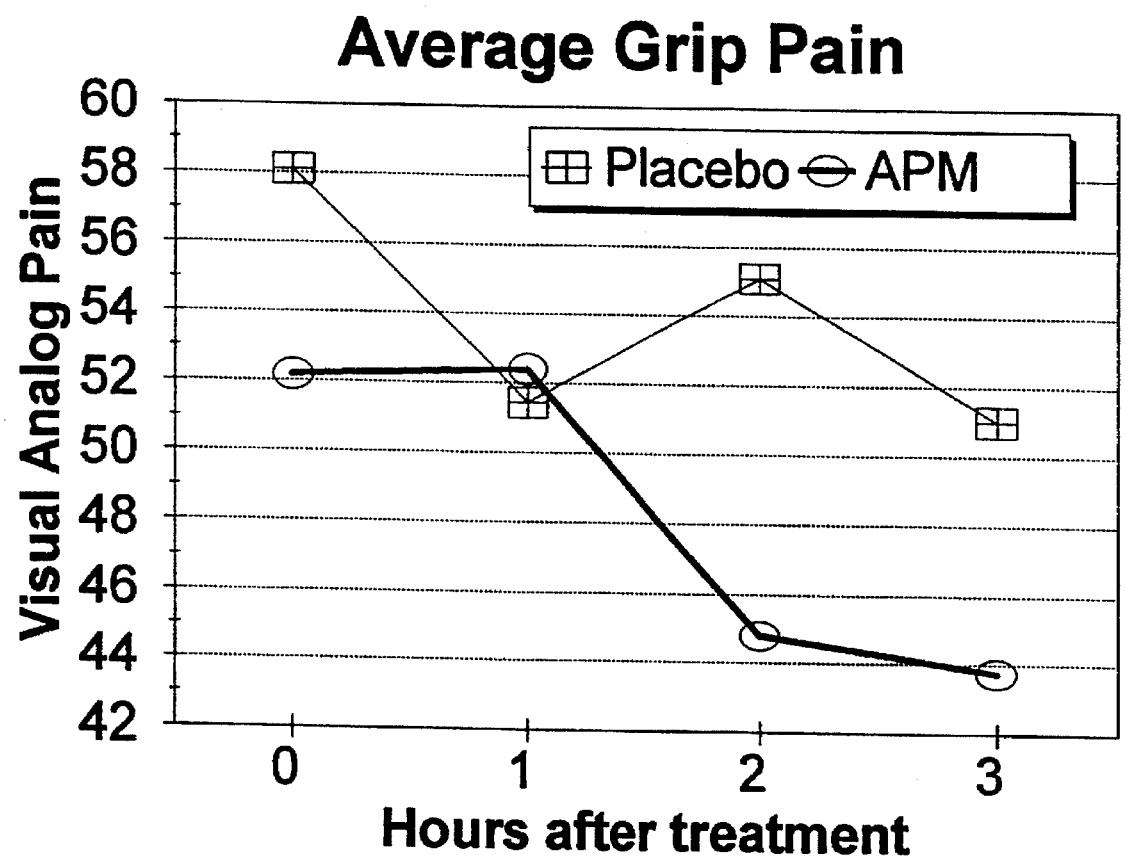
FIG. 8 is a graph depicting the average gripping pain experienced by the APM and control treatment groups measured over time.

To determine average grip pain, a visual analog pain assessment was performed prior to the baseline gripping measurement and then repeated after each subsequent gripping measurement. In Table IX and FIG. 8, the mean data shows that within 2 hours after treatment, grip pain for both APM groups fell at or below the pre-gripping baseline assessment, while both control groups stayed at least 8% higher than the pre-gripping baseline assessment.

TABLE VIII

Grip Strength with and without APM

| Subject # | Grip Strength (mmHg) Hours after Treatment | | | |
|---|---|---|---|---|
| | 0 | 1 | 2 | 3 |
| Control group - 4 tablets placebo | | | | |
| 1 | 275 | 280 | 265 | 260 |
| 2 | 135 | 110 | 105 | 105 |
| 3 | 175 | 170 | 180 | 170 |
| 4 | 165 | 180 | 160 | 170 |
| 5 | 170 | 195 | 195 | 180 |
| 6 | 140 | 155 | 145 | 200 |
| 7 | 95 | 80 | 95 | 95 |
| 8 | 225 | 235 | 245 | 275 |
| 9 | 195 | 205 | 205 | 245 |
| 10 | 230 | 230 | 235 | 225 |
| 11 | 155 | 160 | 145 | 160 |
| mean | 178.18 | 181.82 | 179.55 | 189.67 |
| APM group - 4 tablets APM | | | | |
| 1 | 240 | 235 | 255 | 250 |
| 2 | 65 | 85 | 80 | 105 |
| 3 | 75 | 135 | 155 | 180 |
| 4 | 115 | 135 | 165 | 145 |
| 5 | 140 | 165 | 170 | 160 |
| 6 | 120 | 100 | 140 | 160 |
| 7 | 95 | 110 | 95 | 105 |
| 8 | 190 | 240 | 215 | 210 |
| 9 | 270 | 275 | 295 | 265 |
| 10 | 170 | 165 | 155 | 155 |
| 11 | 180 | 170 | 170 | 170 |
| mean | 150.91 | 165.00 | 172.27 | 173.18 |
| Control group 8 tablets placebo | | | | |
| 12 | 85 | 90 | 100 | 100 |
| 13 | 155 | 155 | 170 | 160 |
| 14 | 165 | 160 | 145 | 135 |
| 15 | 150 | 140 | 145 | 140 |
| 16 | 230 | 210 | 210 | 215 |
| 17 | 180 | 180 | 190 | 225 |
| 18 | 165 | 150 | 170 | 165 |
| 19 | 85 | 90 | 105 | 85 |
| 20 | 55 | 75 | 90 | 90 |
| mean | 141.11 | 138.89 | 147.22 | 146.11 |
| APM group - 8 tablets APM | | | | |
| 12 | 80 | 90 | 95 | 95 |
| 13 | 145 | 160 | 160 | 165 |
| 14 | 125 | 125 | 120 | 135 |
| 15 | 155 | 165 | 165 | 170 |
| 16 | 235 | 230 | 220 | 225 |
| 17 | 185 | 190 | 195 | 220 |
| 18 | 110 | 130 | 160 | 180 |
| 19 | 110 | 115 | 100 | 95 |
| 20 | 75 | 90 | 85 | 80 |
| mean | 135.56 | 143.89 | 144.44 | 151.67 |
| Total mean score by treatment group | | | | |
| Control | 161.50 | 162.50 | 165.00 | 170.00 |
| APM | 144.00 | 155.50 | 159.75 | 163.50 |

TABLE IX

Grip Pain with and without APM

| Subject # | Grip Pain (relative numerical scale) Hours after Treatment | | | | |
|---|---|---|---|---|---|
| | −1 | 0 | 1 | 2 | 3 |
| Control group - 4 tablets placebo | | | | | |
| 1 | 48 | 79 | 50 | 59 | 51 |
| 2 | — | — | — | — | — |
| 3 | 85 | 25 | 22 | 84 | 84 |
| 4 | 46 | 59 | 21 | 21 | 15 |
| 5 | — | — | — | — | — |
| 6 | 47 | 82 | 105 | 86 | 82 |
| 7 | 75 | 76 | 76 | 100 | 77 |
| 8 | 19 | 19 | 18 | 17 | 16 |
| 9 | 24 | 42 | 42 | 41 | 25 |
| 10 | 43 | 70 | 80 | 87 | 85 |
| 11 | 37 | 54 | 45 | 35 | 45 |
| mean | 47.11 | 56.22 | 51.00 | 58.89 | 53.33 |
| APM group - 4 tablets APM | | | | | |
| 1 | 17 | 45 | 55 | 22 | 19 |
| 2 | — | — | — | — | — |
| 3 | 106 | 106 | 40 | 20 | 10 |
| 4 | 47 | 49 | 33 | 30 | 35 |
| 5 | — | — | — | — | — |
| 6 | 46 | 82 | 106 | 105 | 93 |
| 7 | 40 | 58 | 75 | 75 | 73 |
| 8 | 16 | 19 | 19 | 20 | 17 |
| 9 | 41 | 42 | 23 | 24 | 22 |
| 10 | 71 | 81 | 91 | 95 | 107 |
| 11 | 50 | 53 | 59 | 50 | 63 |
| mean | 48.22 | 59.44 | 55.67 | 49.00 | 48.78 |
| Control group - 8 tablets placebo | | | | | |
| 12 | 16 | 48 | 46 | 38 | 17 |
| 13 | 23 | 49 | 36 | 23 | 51 |
| 14 | 35 | 71 | 92 | 132 | 97 |
| 15 | 64 | 66 | 27 | 32 | 57 |
| 16 | 48 | 47 | 47 | 48 | 51 |
| 17 | 14 | 8 | 11 | 8 | 8 |
| 18 | 103 | 128 | 94 | 101 | 84 |
| 19 | 41 | 72 | 73 | 40 | 57 |
| 20 | 43 | 51 | 41 | 40 | 16 |
| mean | 43.00 | 60.00 | 51.89 | 51.33 | 48.67 |
| APM group - 8 tablets APM | | | | | |
| 12 | 16 | 43 | 74 | 39 | 15 |
| 13 | 23 | 23 | 22 | 20 | 20 |

TABLE IX-continued

Grip Pain with and without APM

| | Grip Pain (relative numerical scale) Hours after Treatment | | | | |
|---|---|---|---|---|---|
| Subject # | −1 | 0 | 1 | 2 | 3 |
| 14 | 34 | 31 | 71 | 71 | 72 |
| 15 | 32 | 35 | 40 | 48 | 56 |
| 16 | 18 | 17 | 16 | 20 | 17 |
| 17 | 9 | 13 | 21 | 24 | 7 |
| 18 | 88 | 75 | 90 | 47 | 71 |
| 19 | 98 | 97 | 72 | 74 | 73 |
| 20 | 75 | 70 | 36 | 22 | 17 |
| mean | 43.67 | 44.89 | 49.11 | 40.56 | 38.67 |
| Total mean score by treatment group | | | | | |
| Control | 45.06 | 58.11 | 51.44 | 55.11 | 51.00 |
| APM | 45.94 | 52.17 | 52.39 | 44.78 | 43.72 |

Overall, this study documents that use of APM was successful in relieving pain and that performance was measurably improved. Statistical assessments of measured variables suggests that the inference that the observed differences were due to chance is improbable at p<0.05 to p<0.01 or more.

EXAMPLE 2

Osteoarthritis—Pain Alleviation

The analgesic properties of APM given over time was demonstrated in one osteoarthritic patient engaged in viewing a football game. The patient was in severe pain at the beginning of the game. However, upon consumption of six diet soft drinks through the course of the game (approximately 1 g APM over 3 hours), the patient experienced substantial pain relief and markedly increased joint mobility.

EXAMPLE 3

Multiple Sclerosis—Pain Alleviation

In one example of the analgesic properties of APM in combination with other analgesic agents in relieving pain associated with multiple sclerosis, four tablets each containing 19.5 milligrams of APM was ingested by a patient with multiple sclerosis. The dosage was repeated at 100–120 milligrams every six hours. Upon administration of the APM, the patient's need for opiates for relief from pain dropped by 50%: one-half tablet Percocet (Du Pont Pharmaceuticals, Wilmington, Del.; each tablet containing 5 mg oxycodone hydrochloride and 325 mg acetaminophen) taken 2–3 times a day rather than one tablet taken 4 times a day. By combining APM with the opiate analgesic, the required dosage of the opiate analgesic was decreased, thereby lessening the negative side effects of the opiate analgesic such as constipation experienced by the patient.

EXAMPLE 4

Alleviation of Pain Associated with Injury

APM provided pain relief for a 48 year old female (non-arthritic) who injured her heel and associated tendons and ligaments to the arch of the foot while running along rough terrain. At 12 hours after the injury, the patient walked with a severe limp. Approximately 4 packets (about 0.15 grams) APM mixed in orange juice was given to the patient on an empty stomach. Approximately 50 minutes later, the patient participated in a one mile hike without noticeable limp. A second 4-packet dose in orange juice was administered 5 hours later. Eight hours after start of treatment, the patient was walking without pain. The following morning, there was tenderness to thumb pressure but no pain while walking. Thirty-six hours after treatment, there was no pain and very little tenderness.

EXAMPLE 5

Alleviation of Pain Associated with Back Surgery

Enrolled in a blind study, an osteoarthritis patient was taking a study compound for pain relief. Prior to back surgery, the patient discontinued using the study compound, but postoperatively, he resumed taking five tablets of the study compound unprescribed three times a day. On Day 1 after surgery, the patient took only one prescribed p.r.n. pain tablet and discontinued use of a prescribed PCA pump narcotic pain reliever because he reported a lack of need. Despite continued access to prescribed pain relievers, the patient declined due to lack of need. The patient was walking on Day 1, went home on Day 3, and resumed normal routine without pain on Day 10. The blinded study compound was APM (19.5 milligrams per tablet).

EXAMPLE 6

Myocardial Infraction—Pain Alleviation

Pain associated with myocardial infarction has been associated with platelet aggregation. APM may be used to alleviate pain associated with myocardial infarction.

We claim:

1. A method of decreasing pain in a patient comprising administering to said patient in need of such treatment an effective amount of a composition comprising:

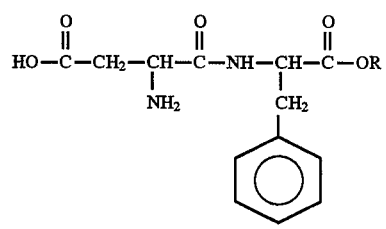

where R is H or an alkyl containing 1 to 6 carbons to effect a reduction in perceived pain by said patient, wherein an effective amount of said composition is from about 80 milligrams to about 320 milligrams.

2. A method of decreasing pain in a patient comprising administering to said patient in need of such treatment an effective amount of a composition comprising:

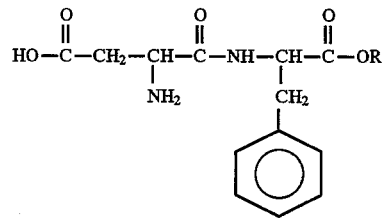

where R is H or an alkyl containing 1 to 6 carbons to effect a reduction in perceived pain by said patient, wherein an effective amount of said composition is about 180 milligrams.

3. A method of decreasing the dosage of a first analgesic medication in a patient for pain, comprising administering to said patient in need of such treatment an effective amount of a second compound comprising:

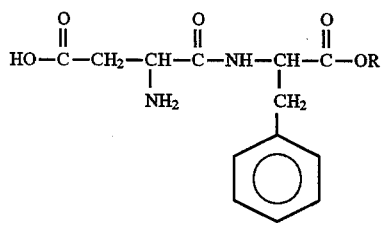

where R is H or an alkyl containing 1 to 6 carbons to cause a reduction in perceived pain by said patient.

4. The method of claim 3, wherein said first analgesic medication is selected from the group consisting of acetaminophen, phenacetin, aspirin, ibuprofen, phenylbutazone, indomethacin and derivatives, opiates and derivatives, piroxacam, and steroidal and nonsteroidal anti-inflammatory agents.

5. The method of claim 3, wherein said effective amount of said second compound is from about 40 milligrams to about 540 milligrams.

6. The method of claim 4, wherein said effective amount of said second compound is from about 40 milligrams to about 540 milligrams.

7. The method of claim 3, wherein an effective amount of said second compound is that amount required to reduce the effective dosage of said first analgesic medication by about 25% to about 75%.

8. The method of claim 4, wherein an effective amount of said second compound is that amount required to reduce the effective dosage of said first analgesic medication by about 25% to about 75%.

9. The method of claim 3, wherein an effective amount of said second compound is that amount required to reduce the effective dosage of said first analgesic medication by about 10% to about 90%.

10. The method of claim 4, wherein an effective amount of said second compound is that amount required to reduce the effective dosage of said first analgesic medication by about 10% to about 90%.

11. A method for treating an osteoarthritis patient for pain, comprising the steps of: administering an effective amount of a composition comprising:

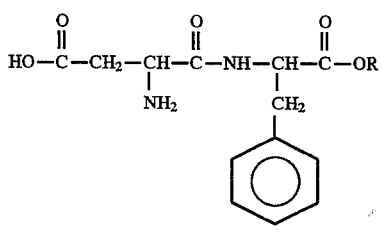

where R is $CH_3$ to effect a reduction in perceived pain by said patient, wherein said composition is the sole active pain-relieving agent administered to said patient.

12. A method of treating pain in a patient comprising administering to said patient in need of such treatment an effective pain-reducing amount of an active pain-relieving agent, wherein said active pain-relieving agent consists of a composition of the formula:

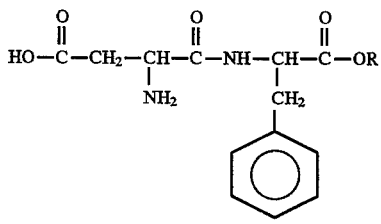

where R is $CH_3$.

13. The method of claim 12, wherein said effective amount is greater than 40 mg.

14. The method of claim 12, wherein said effective amount is from about 80 mg to about 540 mg.

* * * * *

UNITED STATES PATENT AND TRADEMARK OFFICE
CERTIFICATE OF CORRECTION

PATENT NO. : 5,654,334
DATED : August 5, 1997
INVENTOR(S) : Allen B. Edmundson and Carl V. Manion It is certified that error appears in the above-indentified patent and that said Letters Patent is hereby corrected as shown below:

Column 9, line 59, after "8-tablet APM group, a", delete --5--.

Column 10, line 57, Table V, APM groups - 4 or 8 tablets APM, Subject 11, column 2, change "-9" to --9--.

Column 16, line 26, change "Infraction" to --Infarction--.

Signed and Sealed this

Twenty-fourth Day of March, 1998

Attest:

BRUCE LEHMAN

*Attesting Officer*     *Commissioner of Patents and Trademarks*